(12) United States Patent
Tomaioulo

(10) Patent No.: US 7,012,170 B1
(45) Date of Patent: Mar. 14, 2006

(54) PUNCTURE WOUND BANDAGE

(76) Inventor: Theodore B. Tomaioulo, 114 Bohemia St., Plainville, CT (US) 06062

( * ) Notice: Subject to any disclaimer, the term of this patent is extended or adjusted under 35 U.S.C. 154(b) by 0 days.

(21) Appl. No.: 10/989,626

(22) Filed: Nov. 16, 2004

(51) Int. Cl.
*A61F 13/00* (2006.01)
*A61F 15/00* (2006.01)

(52) U.S. Cl. ............................. 602/57; 602/58; 602/41; 602/42

(58) Field of Classification Search ............ 602/41–43, 602/48, 57, 58; 424/443–449; 206/440–441
See application file for complete search history.

(56) References Cited

U.S. PATENT DOCUMENTS

| | | | |
|---|---|---|---|
| 2,391,301 A | | 12/1945 | Dukehart, Jr. ............... 221/63 |
| 2,432,541 A | * | 12/1947 | McClelland ................ 602/48 |
| 2,464,426 A | | 3/1949 | Williams .................... 221/58 |
| 2,721,550 A | | 10/1955 | Banff ......................... 206/441 |
| 2,793,745 A | | 5/1957 | Cox, Jr. ...................... 206/441 |
| 3,189,219 A | | 6/1965 | Holtzworth et al. ........ 221/131 |
| 3,245,855 A | | 4/1966 | Stenvall ...................... 156/152 |
| 3,612,265 A | | 10/1971 | Dickerson .................. 206/441 |
| 3,835,992 A | | 9/1974 | Adams, IV ................. 206/390 |
| 3,899,077 A | | 8/1975 | Spiegelberg ................ 206/441 |
| 4,413,621 A | * | 11/1983 | McCracken et al. .......... 602/52 |
| 4,512,462 A | | 4/1985 | Dills ........................... 206/53 |
| 4,549,653 A | | 10/1985 | Lauritzen .................... 206/441 |
| 4,807,613 A | * | 2/1989 | Koehnke et al. .............. 602/57 |
| 4,858,604 A | * | 8/1989 | Konishi ........................ 602/57 |
| 4,917,929 A | | 4/1990 | Heinecke .................... 448/41.4 |
| 5,271,522 A | | 12/1993 | Ko et al. ..................... 221/58 |
| 5,533,962 A | * | 7/1996 | Peterman et al. ............. 602/54 |
| 5,690,610 A | * | 11/1997 | Ito et al. ...................... 602/53 |
| 5,782,786 A | | 7/1998 | Tomaiuolo ................... 602/41 |
| 5,792,092 A | | 8/1998 | Turngren .................... 602/58 |
| 5,981,823 A | * | 11/1999 | Turngren .................... 602/58 |
| 6,010,002 A | | 1/2000 | Petterson .................... 206/441 |
| 6,053,318 A | | 4/2000 | Petterson .................... 206/440 |
| 6,120,792 A | * | 9/2000 | Juni ........................... 424/448 |
| 6,213,343 B1 | | 4/2001 | Damikolas ................... 221/25 |
| 6,297,422 B1 | * | 10/2001 | Hansen et al. ................ 602/57 |
| D472,319 S | | 3/2003 | Oltmann ..................... D24/189 |
| 6,592,889 B1 | * | 7/2003 | Stout et al. .................. 424/443 |
| 6,617,486 B1 | * | 9/2003 | Murata ........................ 602/48 |
| 6,719,137 B1 | | 4/2004 | Dotta ........................ 206/441 |
| 6,755,321 B1 | | 6/2004 | Solovay et al. ............... 221/73 |
| 6,756,519 B1 | | 6/2004 | Johnson et al. ............... 602/58 |

FOREIGN PATENT DOCUMENTS

GB    2148125 A  *  5/1985

* cited by examiner

*Primary Examiner*—Henry Bennett
*Assistant Examiner*—Amanda Wieker
(74) *Attorney, Agent, or Firm*—The Patent Source

(57) ABSTRACT

Advancements in bandages for treating puncture wounds shown and described herein include sealed bandage with flexible adhesive strips disposed on more rigid carriers with at least one separation line. Bending the sealed bandages separates the carrier along the path of the separation line(s) to thereby pull the strip away from the carrier in the vicinity of the separation line such that at least a portion of the carrier may be pulled from the strip and the bandage applied to a patient. This abstract is provided for the sole purpose of complying with the rules requiring an abstract to allow a searcher or other reader to quickly ascertain the subject matter of the technical disclosure contained herein. This abstract is submitted with the express understanding that it will not be used to interpret or to limit the scope or the meaning of the claims.

20 Claims, 4 Drawing Sheets

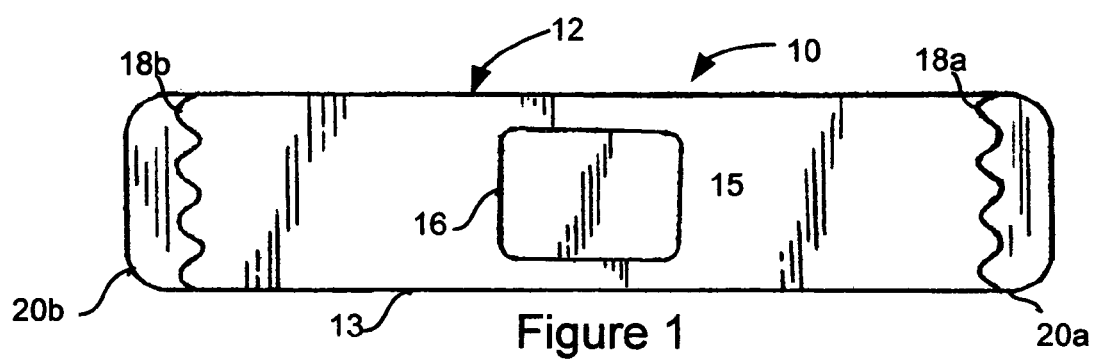
Figure 1
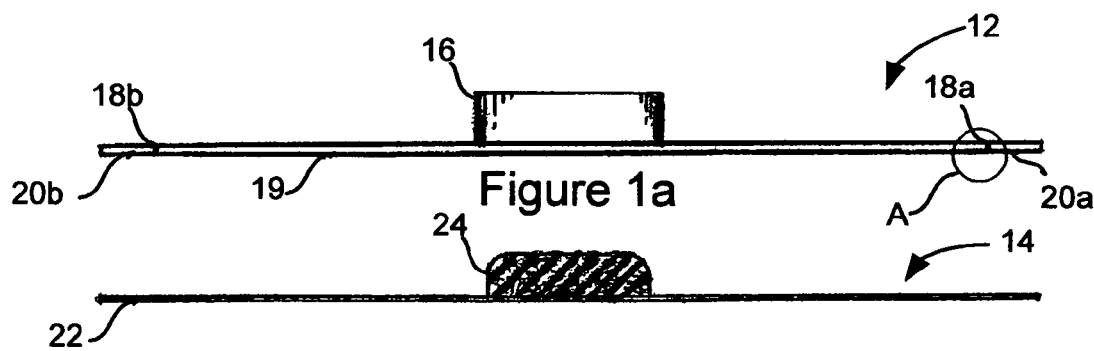
Figure 1a
Figure 1b
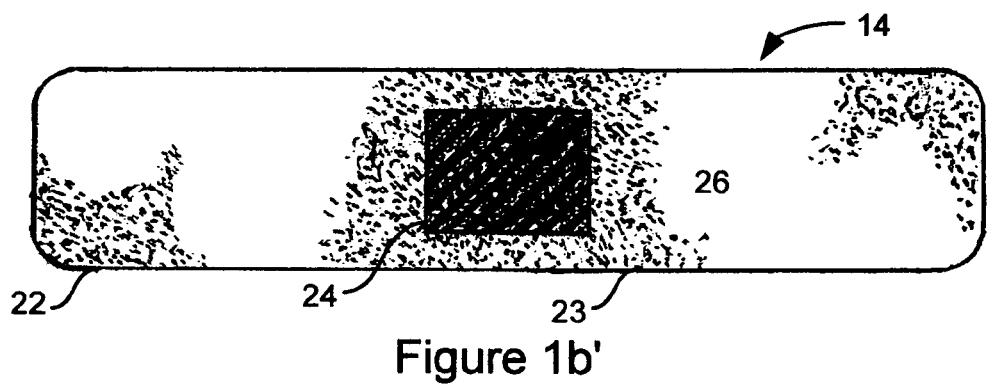
Figure 1b'

PUNCTURE WOUND BANDAGE

BACKGROUND OF THE INVENTION

1. Field of the Invention

The present invention is directed to systems, methods, apparatus and/or devices for dressing human and/or animal wounds. More particularly, the invention relates to the field of dressing puncture wounds with a bandage. Accordingly, the general objects of the invention are to provide novel systems, methods, apparatus and/or devices of such character.

2. Description of the Related Art

Bandages are widely used for the treatment of human and animal wounds of various types. These may include the simple application of gauze, taping gauze over the wound, the application of an adhesive strip bandage, or the application of a specialized bandage designed for a particular application. Although there is a wide range of bandages in use today, the most common dressing for a puncture wound due to the use of a blood withdrawal cannula is still primitive. For example, puncture wounds resulting from medical withdrawal of blood from a patient's inner elbow region are typically simply covered with a folded piece of gauze and held in place by bending the patient's elbow to pinch the gauze between the patient's forearm and upper arm. Naturally, requiring a patient to maintain this position for an extended period of time creates a number of problems. These may include (1) wound infection resulting from gauze contamination before application to the patient; (2) wound infection resulting from a patient's unwillingness and/or inability to maintain this position for a sufficient time; (3) discomfort and/or inconvenience to the patient; and/or (4) untidy disposal of the gauze upon removal, as intended or accidentally. For these and other reasons, such a wound may, instead, be dressed by placing the folded gauze over the puncture wound and then taping the gauze to the patient with one or more strips of medical adhesive tape. While this helps ensure that the gauze remains in place longer, it also creates several problems of it's own. These problems include: (1) the risk that the tape will be inadvertently and/or prematurely pulled loose from the patient; (2) the additional time and expense that a phlebotomist must devote to tape the gauze in place; and/or (3) the risk of wound infection resulting from gauze contamination before application to the patient.

There is, accordingly, a need in the art for novel methods, systems and apparatus for more reliably, efficiently and/or economically dressing puncture wounds. Such methods and apparatus should be well-suited to controlled medical environments such as clinics, hospitals, blood banks, blood drives, medical offices, etc. in which blood is intentionally drawn from patients. Further, such methods and apparatus should also be capable of dressing biopsy wounds. However, such methods and apparatus would also be useful to dress accidental puncture wounds. Such methods and apparatus should solve the above stated deficiencies without introducing additional expense and complexity to the blood-removal process. Accordingly, such methods and apparatus should reduce the risk of contamination, be easy to use and require little, if any, packaging.

SUMMARY OF THE INVENTION

The present invention satisfies the above-stated needs and overcomes the above-stated and other deficiencies of the related art by providing methods, systems and apparatus for safely, efficiently and economically dressing puncture wounds.

One aspect of the present invention is directed to a sealed bandage in which a bandage with an absorbent pad affixed to an adhesive strip is packaged by affixation to a complementary carrier with a blister, to accommodate the pad, and with at least one end region of the bandage as defined by a means for separating (for example, a snap-line) portions of the carrier. The carrier is formed of a material that is substantially more rigid than the adhesive strip and is weakened at the snap-line(s) such that a user may break the carrier along the snap line and peel the carrier from the adhesive strip except for the end region(s) thereof. A snap-line may be shaped in one of a number of configurations, but is preferably shaped to facilitate grasp of the carrier upon breakage along the snap-line.

In a related form, the invention includes a method of dressing a puncture wound that virtually ensures that sterility of the wound and bandage is preserved while applying the bandage to the wound. The inventive method also achieves this benefit while enabling quick and simple application of the bandage. Thus, the invention is particularly well suited for fast-paced and intensive medical environments such as ambulances and hospital emergency rooms. The invention is also well suited for use on intentional wounds occurring during medical procedures performed during routine medical check-ups, blood-work, etc. at offices and/or blood banks. The inventive methods, however, may also be performed on a wide variety of unintentional wounds.

When the invention is applied in a controlled medical environment, methods in accordance with the invention typically commence after insertion of a needle and the withdrawal of blood. In this case, a user, such as a nurse or a phlebotomist, would first grasp the bandage and separate the end(s) of the carrier along the separation lines (for example, by snapping the carrier along pre-weakened stress line(s)) to thereby expose the rigid carrier strip in the vicinity of the separation line(s). The user would then remove the center of the packaging/carrier by grasping and pulling the newly exposed region from the bandage strip. The user may then grasp the remaining end region(s) of the bandage/ carrier and apply the bandage to the desired location without touching the sterile pad of the bandage. If desired, the user may optionally peel the remaining carrier ends off of the bandage strip and press the, thus exposed, adhesive ends of the bandage strip onto the patient. If the bandage is expected to be removed in a short period of time, however, it may be more desirable to leave at least one of the remaining carrier ends on the bandage strip so that it may be easily grasped to remove the bandage from the patient. This is likely to be the case when the bandaged wound is a puncture wound from the intentional withdrawal of blood.

Other important aspects of the invention include the ability to virtually guarantee sterility of the bandage to be used and the minimal amount of packaging needed to provide this benefit. Other benefits of the invention include the monetary savings resulting from the relative ease with which expensive and scarce nurses and phlebotomists may use the inventive bandage since they avoid the need to fuss with complicated packaging, to fold gauze, to tape gauze to a patient, etc.

Naturally, the above-described methods of the invention are particularly well adapted for use with the above-described apparatus of the invention. Similarly, the apparatus of the invention are well suited to perform the inventive methods described above.

Numerous other advantages and features of the present invention will become apparent to those of ordinary skill in the art from the following detailed description of the preferred embodiments, from the claims and from the accompanying drawings.

BRIEF DESCRIPTION OF THE DRAWINGS

The preferred embodiments of the present invention will be described below with reference to the accompanying drawings where like numerals represent like steps and/or structures and wherein:

FIG. 1 is a top plan view of a sealed bandage in accordance with one preferred embodiment of the present invention;

FIG. 1a is a side elevation view of a bandage carrier in accordance with the embodiment of FIG. 1;

FIG. 1b is a side elevation view of a bandage in accordance with the embodiment of FIG. 1;

FIG. 1b' is a top plan view of the bandage of FIG. 1b;

FIG. 3b is a side elevation view of the sealed bandage of FIG. 3a;

FIG. 4b is a partial top plan view of a modified version of the sealed bandage of FIG. 4a.

DETAILED DESCRIPTION OF THE PREFERRED EMBODIMENTS

Figure 1C:
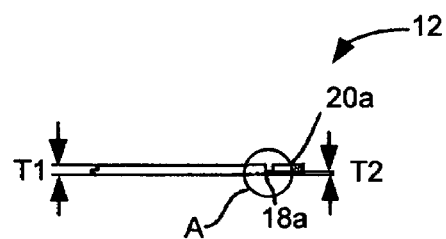
FIG. 1c is a partial side elevation view of the carrier of FIG. 1a illustrating detail A.
Figure 2A:
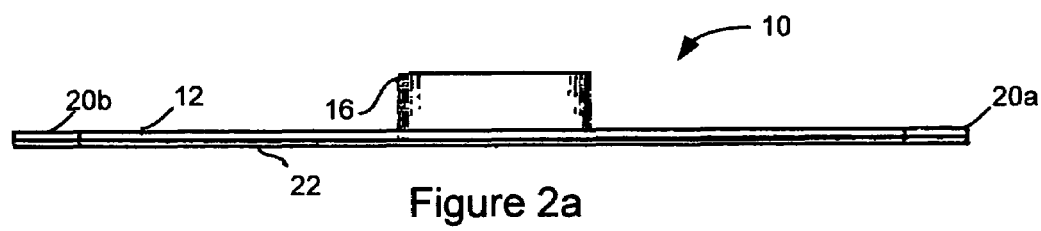
FIGS. 2a through 2d illustrate a method of using the sealed bandage of FIG. 1 in accordance with one preferred method embodiment of the present invention.
Figure 2B:
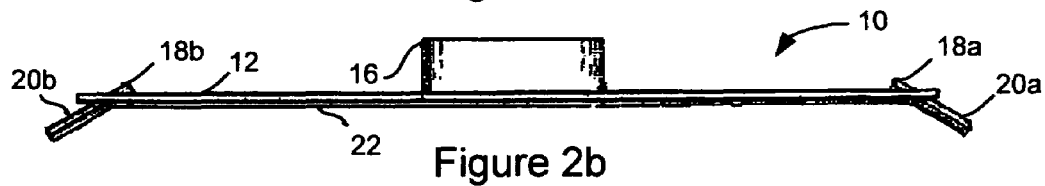
Figure 2C:
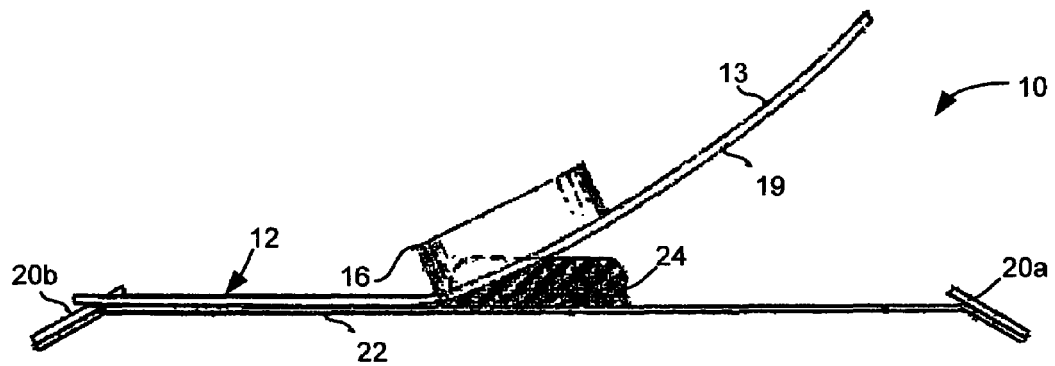
Figure 2D:

A first preferred embodiment of the invention will now be described with joint reference to accompanying FIGS. 1, 1a, 1b, 1b' and 1c. As shown therein, FIG. 1 is a top plan view of a sealed bandage in accordance with one preferred embodiment of the present invention. A side elevation view of the bandage carrier shown in FIG. 1 is illustrated in FIG. 1a. FIG. 1b is a side elevation view of the bandage of FIG. 1. FIG. 1b' is a top plan view of the bandage of FIG. 1b and FIG. 1c is a partial side elevation view of the carrier of FIG. 1a illustrating detail A.

As shown in these Figures, a sealed bandage 10 comprises a carrier 12 and a bandage 14 having an adhesive strip 22 with an adhesive surface 26 that defines an outer perimeter 23. Sealed bandage 10 is preferably about six inches long and between 1 inch and 1¼ inches wide for use as a dressing for a standard needle puncture wound. As discussed herein, the inventive bandage is preferably sized, shaped and constructed so that the bandage may be easily open and applied while wearing rubber gloves of the type normally worn by workers in hospitals and medial offices and clinics. Strip 22 further comprises a pad 24 that is preferable formed of an absorbent gauze or similar material and that is disposed on adhesive surface 26 such that it is disposed inwardly of perimeter 23. In this way adhesive surface 26 surrounds pad 24 to thereby seal pad 24 between strip 22 and carrier 12 in sealed bandage 10. While pad 24 may range in thickness from ⅛ inch to ⅜ inch, it is preferably about ¼ inch thick (see FIG. 1b). As shown in FIG. 1, an outer perimeter 13 of carrier 12 and an outer perimeter 23 of strip 14 are preferably substantially similar and carrier 12 and strip 14 are substantially aligned such that neither extends beyond the other. However, carrier 12 may, optionally, be larger than strip 14 in at least some respects as long as adhesive surface 26 is substantially entirely in contact with a planar surface 19 of carrier 12.

Carrier 12 is preferably elongated and preferably includes first and second weakened snap-lines 18a and 18b that define first and second end regions 20a and 20b between respective ones of snap-lines 18a and 18b and outer perimeter 13 of carrier 12. It will be appreciated that snap-lines 18a and 18b weaken carrier 12 along the path of the snap-lines such that bending sealed bandage 10 will break carrier 12 along the paths of lines 18a and 18b and at least partially pull strip 22 away from carrier 12 in the vicinity of the snap-lines 18a and 18b. As shown in FIG. 1, the snap-lines preferably extend generally transversely to the elongated direction of carrier 12 and preferably follow a path that is at least partially curvilinear. In particular, the path of snap-lines 18a and 18b are preferably sinusoidal. However, such snap-lines may, optionally, follow any of a wide number of alternative paths such as linear (see weakened snap-lines 18a and 18b of FIG. 4a), partially linear and partially curvilinear (see weakened snap-lines 18a''' and 18b''' of FIG. 5), etc. As noted above, sealed bandage 10 can be bent such that carrier 12 will break along snap-lines 18a and 18b and at least partially pull ship 22 away from carrier 12 in the vicinity of the path of the snap-lines. In this way, an intermediate portion 15 of carrier 12 will be exposed to a user's grasp so that it can be pulled away from strip 22 leaving end regions 20a and 20b of carrier 12 adhered to strip 22.

With continuing reference to FIGS. 1 through 1c, carrier 12 preferably further comprises a blister 16 that is sized, shaped and located to seal pad 24 between carrier 12 and strip 22 and to allow planar surface 19 of carrier 12 to adhere to adhesive surface 26 all the way around blister 16. In this way pad 24 is sealed between strip 22 and carrier 12 to ensure sterility of bandage 22 and pad 24 before and upon usage. It will also be appreciated that the bandage configurations shown and described herein provide the additional benefit that they are very inexpensive to store and package because the inventive sealed bandages may be shipped and stored loosely in bulk (such as in a bag or a box) and individually removed from bulk storage upon usage. All of these storage and shipping options are available with little or no risk that the sealed bandages will lose sterility, since they remain individually sealed until the moment before application to a patient. While blister 16 is shown as a substantially rectangular form with rounded corners, those of ordinary skill will readily appreciate that that blister 16 may take some other shape so long as sufficient space is provided to accommodate pad 24. Regardless of the precise shape, carrier 12, including blister 16, is preferably a piece of unitary material that is substantially more rigid than strip 14. In a most preferred embodiment carrier 12 is formed of high density rigid plastic that is approximately 20 mils thick and weakened snap-lines 18a and 18b are preferably about 2 mils thick.

With reference now to FIG. 1c, there is shown therein an expanded partial side elevation view of the carrier of FIG. 1a. As shown in detail A, a thickness T1 represents the total thickness of carrier 12 in the vicinity of weakened line 18a and that a thickness T2 represents the thickness of carrier 12 at weakened line 18a. In a preferred embodiment in which carrier 12 is formed of injection molded plastic, T1 is preferably about 20 mils and T2 is preferably about 2 mils.

A preferred method of using the sealed bandage of FIGS. 1 through 1c, will now be described with joint reference to FIGS. 2a through 2d. As shown therein, when a user wishes to treat a wound on a patient, the user selects a sealed bandage 10 and bends it to thereby snap carrier 12 along first and second snap-lines 18a and 18b while not damaging flexible strip 22. This bending action causes strip 22 to at least partially pull away from carrier 12 in the vicinity of snap-lines. A user then grasps one of end regions 20a and 20b and intermediate region 15 of carrier 12 in the vicinity of the grasped end region and peels intermediate region 15 of carrier 12 off of strip 22 to thereby expose a portion of adhesive surface 26 and pad 24. Finally, a user places bandage 14 on the patient such that pad 24 is applied to the wound and such that the, now exposed, portion of adhesive surface 26 adheres to the patient. After peeling carrier 12 and just prior to placing the bandage on a patient, a user may choose to grasp both end regions of the bandage and pull it taught to help ensure precise application of the bandage onto the wound. Naturally, if reservoir 17 contains any substance (see FIGS. 3a and 3b), that substance will be applied to the wound as pad 24 is applied to the wound. Optionally, reservoir 17 may be sealed to thereby isolate a substance therein. When this is the case, a user may break the seal to thereby force the sealed substance into or onto the adjacent pad. It will be noted that the above-noted method envisions application of bandage 14 to a patient while opposing end portions 20a and 20b of carrier 12 remain adhered to respective end portions of strip 22. This enables the patient to conveniently remove bandage 14 at a later time since the patient may easily grasp the end portions 20a and 20b. This is particularly convenient when the sealed bandage is used to treat a wound caused during a common blood work procedure since the bandage for such a wound is often removed within an hour of completion of the blood work.

Figure 3A:
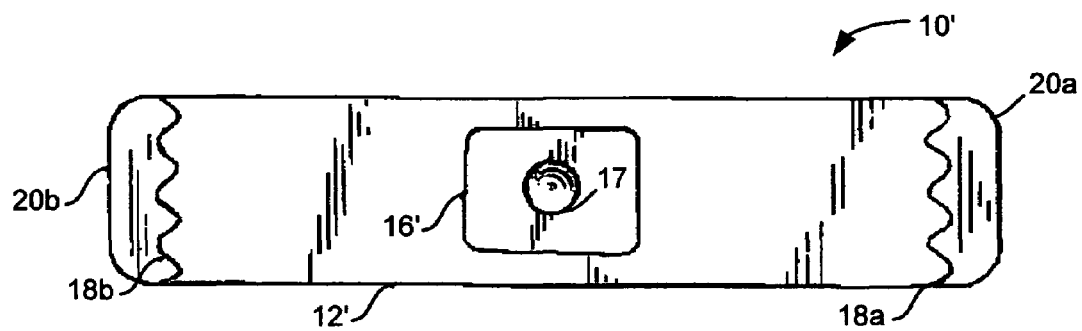
FIG. 3a is a top plan view of a sealed bandage in accordance with an alternative preferred embodiment of the present invention.
Figure 3B:
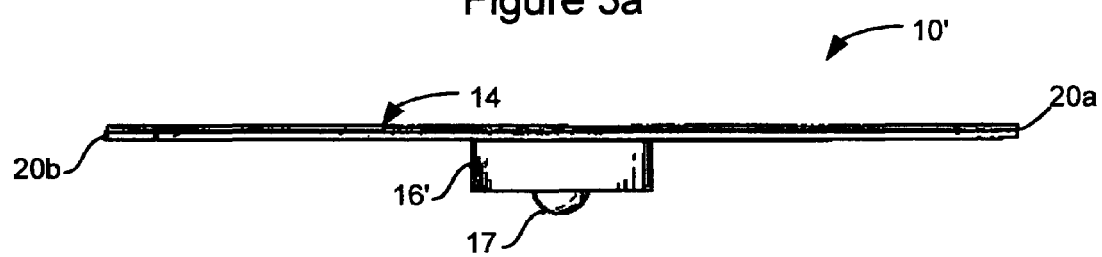

Turning now to FIG. 3a, there is shown therein a top plan view of a sealed bandage 10' in accordance with an alternative preferred embodiment of the present invention. FIG. 3b is a side elevation view of the sealed bandage of FIG. 3a. As shown therein a sealed bandage 10' primarily differs from sealed bandage 10 of FIGS. 1 through 1c in the use of a modified carrier 12' having a blister 16' with a reservoir 17 thereon. As shown, reservoir 17 may accommodate a substance adjacent to pad 24 and is preferably shaped as a portion of a sphere. Such substances may be a solid, a gel, a paste or a fluid and may include an ointment, alcohol, an antibiotic or other medication that is desirous to apply to a patient's wound. The reservoir may be sealed such that the substance will remain in the reservoir until the seal is broken and the substance is disbursed onto or into the pad. Those of ordinary skill will readily appreciate that that reservoir 17 may take some other shape so long as sufficient space is prodded to accommodate the substance to be stored therein. Regardless of the precise shape, carrier 12', including blister 16', reservoir 17, is preferably a piece of unitary material that is substantially more rigid than strip 14.

Figure 4A:
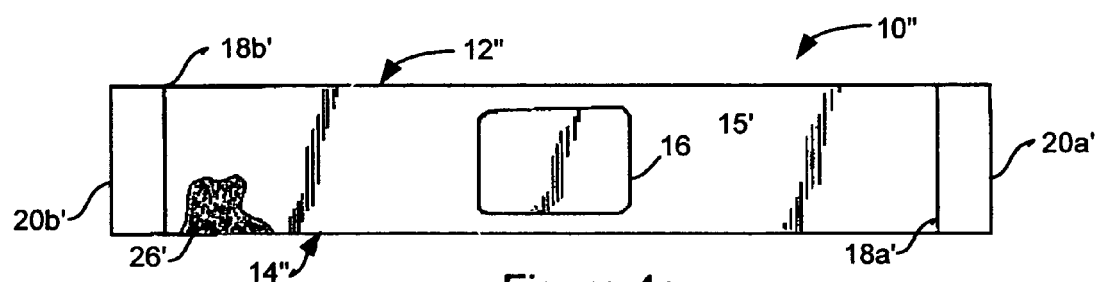
FIG. 4a is a top plan view of a sealed bandage in accordance with yet another alternative preferred embodiment of the present invention.
Figure 4B:
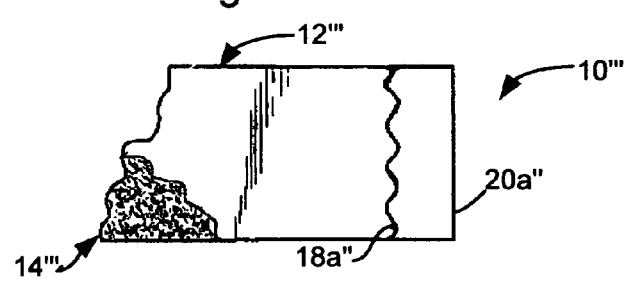

A sealed bandage in accordance with still other alternative preferred embodiments of the present invention is shown in FIGS. 4a and 4b. As shown in FIG. 4a, a sealed bandage 10" primarily differs from sealed bandage 10 of FIGS. 1 through 1c in the shape of weakened lines 18a' and 18b' and in the use of a composite carrier in which intermediate portion 15' of carrier 12" is formed of a different material than end portions 20a' and 20b'. For example, intermediate portion 15' may be formed of plastic while end portions 20a' and 20b' may be formed of paper. Further, FIG. 4b primarily differs from the embodiment of FIG. 4a in the shape of sinusoidal weakened line 18a" and the shape of end region 20a".

Figure 5:
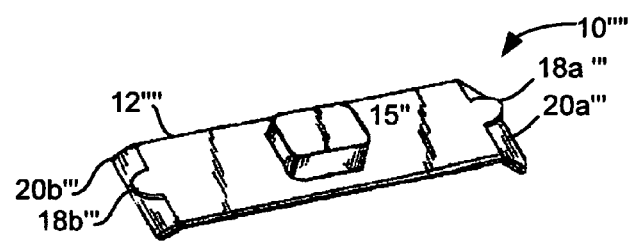
FIG. 5 is a perspective view of a sealed bandage in accordance with still another alternative preferred embodiment of the present invention.

FIG. 5 is a perspective view of a sealed bandage in accordance with still another alternative preferred embodiment of the present invention. As shown therein, a sealed bandage 10"" has previously been bent at end regions 20a'" and 20b'" and primarily differs from sealed bandage 10 of FIGS. 1 through 1c in the use of a carrier 12"" with both linear and curvilinear weakened paths 18a'" and 18b'". This arrangement results in differently shaped end regions 20a" and 20b'" and in substantially semicircular grasping tabs on intermediate portion 15" of carrier 12"".

While the present invention has been described in connection with what is presently considered to be the most practical and preferred embodiments, it is to be understood that the invention is not limited to the disclosed embodiments, but is intended to encompass the various modifications and equivalent arrangements included within the spirit and scope of the appended claims. With respect to the above description, for example, it is to be realized that the optimum dimensional relationships for the parts of the invention, including variations in size, materials, shape, form, function and manner of operation, assembly and use, are deemed readily apparent to one skilled in the art, and all equivalent relationships to those illustrated in the drawings and described in the specification are intended to be encompassed by the appended claims. Therefore, the foregoing is considered to be an illustrative, not exhaustive, description of the principles of the present invention.

What is claimed is:

1. A sealed bandage comprising:
a flexible strip with an adhesive surface that defines an outer perimeter and a pad disposed inwardly of the adhesive surface perimeter; and
a unitary carrier with a generally planar surface at least partially in contact with and adhered to the adhesive surface and defining an outer perimeter, the carrier being substantially more rigid than the strip and having at least one weakened snap-line defining an end region between the snap-line and the planar surface perimeter, the carrier further comprising a blister that is generally sized, shaped and located to enclose the pad and to allow the planar surface adhering to the adhesive surface to surround the blister.

2. The sealed bandage of claim 1 wherein the perimeter of the planar surface substantially corresponds to the perimeter of the flexible strip.

3. The sealed bandage of claim 1 wherein the sealed bandage can be bent such that the carrier will break along the at least one snap-line and pull the strip away from the carrier in the vicinity of the snap-line such that a portion of the carrier can be pulled away from the strip leaving the end region of the carrier adhered to the strip.

4. The sealed bandage of claim 1 wherein the flexible strip and the carrier are generally elongated and wherein the snap-line generally extends transverse to the elongated direction of the carrier.

5. The sealed bandage of claim 4 wherein the snap-line is at least partially curvilinear.

6. The sealed bandage of claim 5 wherein the snap-line is sinusoidal.

7. The sealed bandage of claim 5 wherein the snap-line comprises both linear and curvilinear portions.

8. The sealed bandage of claim 4 wherein the snap-line is linear.

9. The sealed bandage of claim 1 wherein the blister further comprises a reservoir for accommodating fluid adjacent to the pad.

10. The sealed bandage of claim 1 wherein
the flexible strip and the carrier are generally elongated;
the at least one snap-line comprises a first weakened snap-line defining a first end region between the first snap-line and the perimeter of the planar surface and a second weakened snap-line defining a second end region between the second snap-line and the perimeter of the planar surface, the first and second end regions being located at the opposing ends of the planar surface.

11. A sealed bandage comprising:
a flexible strip with an adhesive surface that defines an outer perimeter and a pad disposed inwardly of the adhesive surface perimeter, and
a generally rigid carrier having a substantially planar surface in contact with and adhered to the adhesive surface , the carrier further comprising means for sealing the pad between the strip and the carrier, means for separating the carrier along a first predetermined path such that bending the sealed bandage will separate the carrier along the first path and at least partially pull the strip away from the carrier in the vicinity of the means for separating, and means for Separating the carrier along a second predetermined path such that bending the sealed bandage will separate the carrier along the second path and at least partially pull the strip away from the carrier in the vicinity of the means for separating, wherein the first and second means for separating are located at opposite sides of the pad.

12. The sealed bandage of claim 11 wherein the flexible strip and the carrier are generally elongated and wherein the path is generally transverse to the elongated direction of the carrier.

13. The sealed bandage of claim 11 wherein
the first means for separating comprises a first weakened snap-line defining a first end region between the first snap-line and the perimeter of the planar surface; and
the second means for separating comprises a second weakened snap-line defining a second end region between the second snap-line and the perimeter of the planar surface.

14. The sealed bandage of claim 13 wherein the first weakened snap-line is at least partially curvilinear.

15. The sealed bandage of claim 13 wherein the sealed bandage can be bent such that the carrier will break along the first and second snap-lines and the portion of the carrier therebetween can be pulled away from the strip leaving the first and second end regions of the carrier adhered to the strip.

16. A method of treating a patient's wound with a bandage of the type having a flexible strip with an adhesive surface and a rigid carrier with a generally planar surface at least partially in contact with and adhered to the adhesive surface, the strip having a pad sealed between the carrier and the strip and the carrier having first and second weakened snap-lines defining first and second end regions with an intermediate region therebetween, the method comprising:
bending the sealed bandage to thereby snap the carrier along the first and second snap-lines and at least partially pull the strip away from the carrier in the vicinity of the snap-lines;
grasping one of the end regions and the intermediate region of the carrier in the vicinity of the grasped end region;
peeling the intermediate region of the carrier off of the strip to there by expose a portion of the adhesive surface and the pad; and
placing the bandage on the patient such that the pad is applied to the wound and the exposed portion of the adhesive surface adheres to the patient.

17. The method of claim 16 further comprising the step of grasping both end regions of the bandage after the step of peeling and before the step of placing.

18. The method of claim 16 further comprising the steps of:
grasping one of the end regions after the step of placing; and
pulling the bandage off of the patient.

19. The method of claim 16 further comprising the step of peeling the end regions of the carrier off of the strip to thereby expose additional portions of the adhesive surface.

20. The method of claim 16 wherein:
the step of peeling further comprises leaving the end regions of the carrier adhered to the strip;
the step of placing further comprises placing the bandage on the patient such that the end regions can not adhere to the patient; and
the method further comprises grasping at least one end region and pulling the at least one grasped end region to thereby pull the bandage off of the patient.

* * * * *